United States Patent [19]
Kübbeler et al.

[11] 4,319,038
[45] Mar. 9, 1982

[54] PRODUCTION OF 1,1-DIACETOXYETHANE

[75] Inventors: Hans-Klaus Kübbeler, Swisttal; Heinz Erpenbach, Cologne; Klaus Gehrmann, Erftstadt; George Kohl, Hürth, all of Fed. Rep. of Germany

[73] Assignee: Hoechst Aktiengesellschaft, Fed. Rep. of Germany

[21] Appl. No.: 195,480

[22] Filed: Oct. 9, 1980

[30] Foreign Application Priority Data

Oct. 11, 1979 [DE] Fed. Rep. of Germany ....... 2941232

[51] Int. Cl.³ .................. C07C 67/36; C07C 67/37; C07C 69/16
[52] U.S. Cl. .................. 560/232; 260/546; 260/549; 562/517
[58] Field of Search .................. 560/232

[56] References Cited

FOREIGN PATENT DOCUMENTS 2610035 9/1976 Fed. Rep. of Germany ...... 560/263

Primary Examiner—Vivian Garner
Attorney, Agent, or Firm—Connolly and Hutz

[57] ABSTRACT

The invention relates to an improved process for making 1,1-diacetoxyethane by reacting methyl acetate and/or dimethylether with carbon monoxide and hydrogen under practically anhydrous conditions, at temperatures of 350° to 575° K., under pressures of 1 to 300 bars, and in the presence of a catalyst system containing noble metals belonging to group VIII of the periodic system of the elements, or compounds thereof, and iodine and/or its compounds. The improved process is effected in the presence of a catalyst system containing, as additional ingredients, an aliphatic carboxylic acid having 1 to 8 carbon atoms, a heterocyclic aromatic compound, in which at least one hetero atom is a quaternary nitrogen atom, and a manganese or rhenium compound.

3 Claims, 1 Drawing Figure

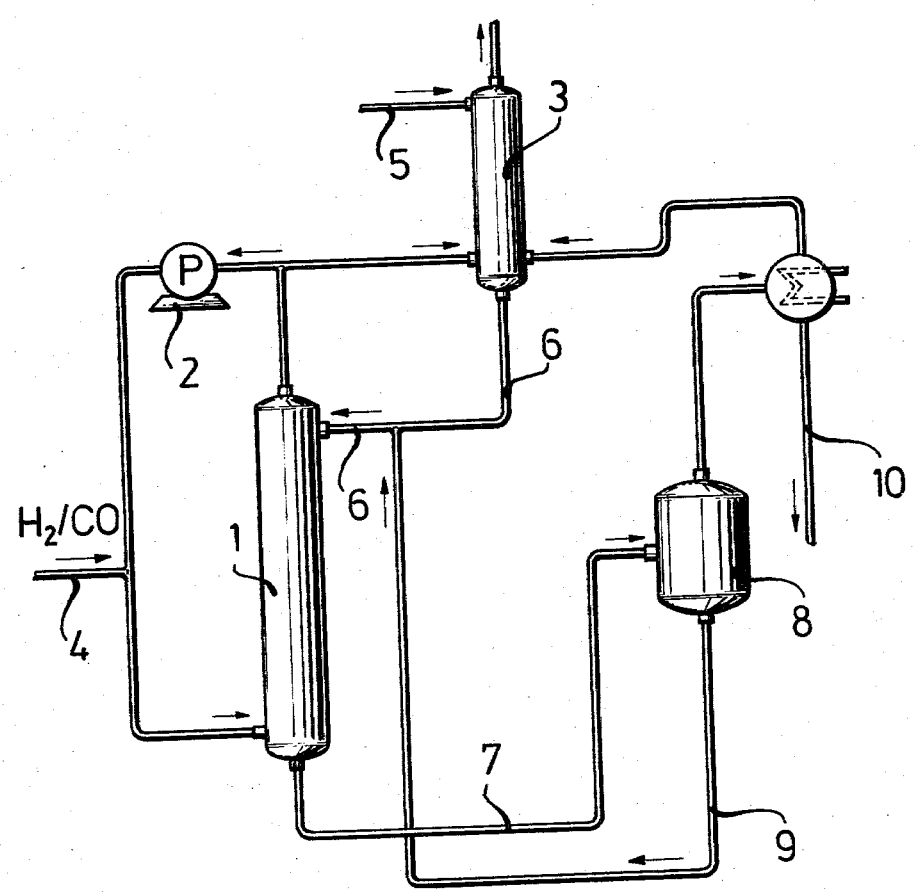

PRODUCTION OF 1,1-DIACETOXYETHANE

The present invention relates to a process for making 1,1-diacetoxyethane (ethylidene diacetate) by reacting methyl acetate and/or dimethylether with carbon monoxide and hydrogen under practically anhydrous conditions, at temperatures of 350° to 575° K., under pressures of 1 to 300 bars, and in the presence of a catalyst system containing noble metals belonging to group VIII of the periodic system of the elements, or compounds thereof, and iodine and/or its compounds, the process comprising: effecting the reaction in the presence of a catalyst system containing, as additional ingredients, an aliphatic carboxylic acid having 1 to 8 carbon atoms, a heterocyclic aromatic compound, in which at least one hetero atom is a quaternary nitrogen atom, and a manganese or rhenium compound.

A comparable process for making 1,1-diacetoxyethane (ethylidene diacetate) has been described in German Patent Specification "Offenlegungsschrift" No. 2 610 035, wherein, however, the noble metal belonging to group VIII of the periodic system of the elements and an iodide are used in combination with a multiple promoter containing at least one member selected from the group consisting of chromium, cobalt, iron and nickel, and a organophosphine, organoarsine, organostibine, organonitrogen and/or organophosphorus compound.

The process disclosed in German Patent Specification "Offenlegungsschrift" No. 2 610 035 is seriously handicapped by the fact that the metal compounds and secondary products of the multiple promoter are substantially insoluble in 1,1-diacetoxyethane, so that the circulation of the catalyst-system, which is necessary for continuous operation, is rendered very difficult or even impossible. In addition to this, the above insoluble compounds have been found unduly to affect the separation of 1,1-diacetoxyethane from the catalyst-system. As a result, it is necessary for the expensive noble metal-containing catalyst to be subjected to cumbersome intermediate processing treatment with undesirable loss of valuable catalyst and rapid adverse effects on the activity of the entire system. These are the reasons why the process just described has not been commercialized heretofore. Still further, the use of chromium as a promoter under conditions comparable with those disclosed in the working examples of German Patent Specification "Offenlegungsschrift" No. 2 610 035 has been found significantly to impair the catalyst efficiency in respect of 1,1-diacetoxyethane, and favor the formation of acetic anhydride.

The process of this invention has unexpectedly been found significantly to increase the catalyst activity, expressed in grams 1,1-diacetoxyethane and acetic anhydride obtained per gram noble metal per hour, the selective formation of 1,1-diacetoxyethane remaining practically unchanged.

This is more especially an unexpected result inasmuch as the compounds of manganese and rhenium would not have been expected to be soluble in the reaction system in the absence of any indication in the prior literature that manganese and rhenium compounds indeed have an activity-increasing effect in the hydrogenating carbonylation of esters and/or ethers.

Manganese and rhenium compounds useful in the process of this invention comprise, e.g. manganese acetate, manganese chloride, manganese iodide, manganese carbonyl, cyclopentadienylmanganese tricarbonyl, rhenium chloride, rhenium oxychloride, rhenium decacarbonyl.

The present invention also avoids the adverse effects which are associated with the process described in German Patent Application "Offenlegungsschrift" No. 2 610 035 in view of the following fact:

Both under the reaction conditions and the conditions selected for the work-up of the products obtained by the hydrogenating carbonylation of methyl acetate and dimethylether, respectively, the heterocyclic aromatic compounds with at least one quaternary nitrogen as the hetero atom, which are used individually or in combination, are in the form of a melt which is a suitable solvent for the noble metal complexes and for the manganese or rhenium compounds and is also readily miscible with 1,1-diacetoxyethane.

Further preferred features of the present invention provide:

(a) for the heterocyclic compounds used to have a melting point or mixed melting point of less than 410° K.;

(b) for the heterocyclic compounds to be used in the form of their addition products with acetic acid or methyl iodide;

(c) for the catalyst system comprised of noble metal (compound)/manganese or rhenium compound/iodine (compound)/carboxylic acid/heterocyclic compound to be used in an atomic or molar ratio of 1:(0.1–10):(1–1400):(10–2000):(1–1200); and (d) for a carbon monoxide/hydrogen mixture containing 25 to 75 volume % hydrogen to be used.

Useful heterocyclic aromatic compounds which have the properties necessary in accordance with this invention comprise, for example:

(1) N-methylpyridinium iodide; N,N-dimethylimidazolium iodide; N-methyl-3-picolinium iodide; N-methyl-2,4-lutidinium iodide; N-methyl-3,4-lutidinium iodide; N-methyl-quinolinium iodide;

(2) pyridinium acetate; N-methylimidazolium acetate; 3-picolinium acetate; 2,4-lutidinium acetate; 3,4-lutidinium acetate.

The promoter properties of these addition products are considerably improved in the presence of an aliphatic carboxylic acid with 1 to 18 carbon atoms.

The process of the present invention should preferably be effected at temperatures of 400° to 475° K. and under pressures of 20 to 150 bars. It is also preferable to use 0.0001 to 0.01 mol of the noble metal belonging to group VIII of the periodic system of the elements or its compounds per mol of methyl acetate and/or dimethylether. Further preferred features provide for the catalyst system of noble metal (compound)/manganese or rhenium compound/iodine (compound)/carboxylic acid/heterocyclic compound to be used in an atomic or molar ratio of 1:(0.5–8):(10–300):(25–600):(10–300), and for acetic acid to be used as the carboxylic acid.

The present process which should preferably be carried out in liquid phase, can be effected in a single or in a plurality of reaction zones, which may be series-connected, i.e., one downstream of another, or parallel with one another. It is possible for the present process to be effected continuously or discontinuously. The reaction zone is preferably constituted by one or more autoclaves, one or more relatively long tubular reactors, which may be arranged parallel with one another. The reaction zone should be made of material which is inert with respect to the reaction media, and has the thickness necessary to remain unaffected by the reaction temperature and pressure. Use should more preferably be made of stainless steel materials, such as Hastelloy type B and C, respectively, or of zirconium-lined reactors. The reaction zone should preferably be provided with heat exchangers, which may be arranged inside or outside the reaction zone and permit the reaction temperature to be maintained constant. Gas and liquid phase are thoroughly mixed by means of an agitator or by enforced circulation of the liquid reaction media.

The invention will now be described with reference to the accompanying diagrammatic representation showing a typical form of flow scheme for carrying out the present process.

Methyl acetate and/or dimethylether is placed in an autoclave 1 made up of Hastelloy C and reacted therein with a mixture of carbon monoxide and hydrogen to give 1,1-diacetoxyethane, the reaction being effected under a preferred pressure of 20 to 150 bars, at a preferred temperature of 400° to 475° K., and in the presence of a catalyst system comprised of one or more noble metals belonging to group VIII of the periodic system of the elements or their compounds and iodine and/or its compounds, preferably methyl iodide, with addition of one or more manganese or rhenium compounds, and in the presence of a carboxylic acid, preferably acetic acid, and at least one heterocyclic aromatic compound, in which at least one hetero atom is a quaternary nitrogen atom.

The bulk of unreacted carbon monoxide and hydrogen is circulated by means of a gas recirculation pump 2, whilst a fraction thereof is allowed to issue from the system via a scrubbing stage 3. Fresh carbon monoxide and hydrogen are introduced into the gas under circulation via a conduit 4 in metered proportions corresponding to the conversion rate. Fresh methyl acetate and/or dimethylether are supplied in quantities corresponding to the conversion rate via a conduit 5 opening into the upper portion of the scrubbing stage 3 and introduced into the reactor 1 through a conduit 6. The reaction mixture issues from the reactor 1 through a conduit 7. The distilling column 8 is used to effect the separation of non volatile constituents of the catalyst system, which are recycled to the reactor 1 via conduits 9 and 6. Condensate obtained through conduit 10 is subjected to distillative treatment in a work-up stage which does not form part of the present process. Unreacted feed material and an acetic acid proportion corresponding to that contained in the catalyst system are recycled to the reactor 1. 1,1-Diacetoxyethane and acetic anhydride are obtained together with acetic acid as the reaction products. They are analyzed by gas-chromatography and NMR-spectroscopy and ultimately separated from each other by customary fractional distillation.

The following Examples illustrate the invention:

EXAMPLE 1

(Outside invention)

250 g methyl acetate, 1.6 g $RhCl_3.3H_2O$, 50 g $CH_3I$, 25 g acetic acid and 68 g N,N-dimethylimidazolium iodide were placed in a Hastelloy autoclave and reacted therein under total pressure of 100 bars at 435° K. with a mixture of 60 volume % CO and 40 volume % $H_2$. After a reaction period of 23 minutes, 109 g of a mixture of 60 mass % 1,1-diacetoxyethane and 40 mass % acetic anhydride was obtained from the reaction mixture. This corresponded to a catalyst efficiency of 271 g 1,1-diacetoxyethane per g Rh per hour and 183 g acetic anhydride per gram Rh per hour.

EXAMPLE 2

(Outside invention)

250 g methyl acetate, 1.6 g $RhCl_3.3H_2O$, 5.4 g $Cr(CO)_6$, 50 g $CH_3I$, 25 g acetic acid and 68 g N,N-dimethylimidazolium iodide were placed in a Hastelloy autoclave and reacted therein under a total pressure of 100 bars at 435° K. with a mixture of 60 volume % CO and 40 volume % $H_2$. After a reaction period of 20 minutes, 146 g of a mixture of 37.7 mass %, 1,1-diacetoxyethane and 62.3 mass % acetic anhydride was obtained from the reaction mixture. This corresponded to a catalyst efficiency of 264 g 1,1-diacetoxyethane per gram Rh per hour and 436 g acetic anhydride per gram Rh per hour.

EXAMPLE 3

250 g methyl acetate, 1.6 g $RhCl_3.3H_2O$, 4 g $Mn(OAc)_2.4H_2O$, 50 g $CH_3I$, 25 g acetic acid and 68 g N,N-dimethylimidazolium iodide were placed in a Hastelloy autoclave and reacted therein under a total pressure of 100 bars at 435° K. with a mixture of 60 volume % CO and 40 volume % $H_2$. After a reaction period of 20 minutes, 141 g of a mixture of 58.7 mass % 1,1-diacetoxyethane and 41.3 mass % acetic anhydride was separated from the reaction product. This corresponded to a catalyst efficiency of 397 g 1,1-diacetoxyethane per gram Rh per hour and 279 g acetic anhydride per gram Rh per hour.

EXAMPLE 4

250 g methyl acetate, 1.6 g $RhCl_3.3H_2O$, 3.9 g $Re_2(CO)_{10}$, 50 g $CH_3I$, 25 g acetic acid and 68 g N,N-dimethylimidazolium iodide were placed in a Hastelloy autoclave and reacted therein under a total pressure of 100 bars at 435° K. with a mixture of 60 volume % CO and 40 volume % $H_2$. After a reaction period of 17 minutes, 145 g of a mixture of 60.9 mass %, 1,1-diacetoxyethane and 39.1 mass % acetic anhydride was obtained from the reaction product. This corresponded to a catalyst efficiency of 498 g 1,1-diacetoxyethane per gram Rh per hour and 320 g acetic ahydride per gram Rh per hour.

EXAMPLE 5

250 g methyl acetate, 1 g $RhCl_3.3H_2O$, 1 g $RuCl_3.3H_2O$, 4 g $Mn(OAc)_2.4H_2O$, 70 g $CH_3I$, 30 g acetic acid and 80 g N,N-dimethylimidazolium iodide were placed in a Hastelloy autoclave and reacted therein under a pressure of 80 bars at 440° K. with a mixture of 60 volume % CO and 40 volume % $H_2$. After a reaction period of 20 minutes, 151 g of a mixture of 62.8 mass %, 1,1-diacetoxyethane and 37.2 mass % acetic anhydride was separated from the reaction product. This corresponded to a catalyst efficiency of 728 g 1,1-diacetoxyethane per gram Rh per hour and 431 g $Ac_2O$/g Rh per hour.

EXAMPLE 6

250 g methyl acetate, 2.5 g $(NH_4)_2IrCl_6$, 4 g $Mn(OAc)_2.4H_2O$, 60 g $CH_3I$, 30 g acetic acid and 60 g N,N-dimethylimidazolium iodide were placed in a Hastelloy autoclave and reacted therein under a pressure of 80 bars at 450° K. with a mixture of 60 volume % CO and 40 volume % $H_2$. After a reaction period of 26 minutes, 139 g of a mixture of 59.3 mass % 1,1-diacetoxyethane and 40.7 mass % acetic anhydride was separated from the reaction product. This corresponded to a catalyst efficiency of 175 g 1,1-diacetoxyethane per gram Ir per hour and 120 g Ac$_2$O per gram Ir per hour.

EXAMPLE 7

250 g dimethylether, 1.8 g RhCl$_3$.3H$_2$O, 6 g Mn(OAc)$_2$.4H$_2$O, 70 g CH$_3$I, 80 g acetic acid and 70 g N,N-dimethylimidazolium iodide were placed in a Hastelloy autoclave and reacted therein under a pressure of 80 bars at 440° K. with a mixture of 60 volume % CO and 40 volume % H$_2$. After a reaction period of 16 minutes, 149 g of a mixture of 58.1 mass % 1,1-diacetoxyethane and 41.9 mass % acetic anhydride was separated from the reaction product. This corresponded to a catalyst efficiency of 461 g 1,1-diacetoxyethane per gram Rh per hour and 333 g Ac$_2$O per gram Rh per hour.

EXAMPLE 8

250 g methyl acetate, 1.8 g RhCl$_3$.3H$_2$O, 6 g Mn(OAc)$_2$.4H$_2$O, 70 g CH$_3$I, 30 g acetic acid, 60 g acetic anhydride and 100 g N,N-dimethylimidazolium iodide were placed in a Hastelloy autoclave and reacted therein under a pressure of 80 bars at 440° K. with a mixture of 60 volume % CO and 40 volume % H$_2$. After a reaction period of 19 minutes, 241 g of a mixture of 67.2 mass % 1,1-diacetoxyethane and 32.8 mass % acetic anhydride was separated from the reaction product. This corresponded to a catalyst efficiency of 727 g 1,1-diacetoxyethane per gram Rh per hour and 85.5 g Ac$_2$O per gram Rh per hour.

EXAMPLE 9

250 g methyl acetate, 0.8 g RhCl$_3$.3H$_2$O, 5 g MnCl$_2$.4H$_2$O, 80 g CH$_3$I, 40 g acetic acid and 120 g N-methyl-3-picolinium iodide were placed in a Hastelloy autoclave and reacted therein under a pressure of 70 bars at 440° K. with a mixture of 60 volume % CO and 40 volume % H$_2$. After a reaction period of 21 minutes, 153 g of a mixture of 63.1 mass % 1,1-diacetoxyethane and 38.7 mass % acetic anhydride was separated from the reaction product. This corresponded to a catalyst efficiency of 857 g 1,1-diacetoxyethane per gram Rh per hour and 541 g Ac$_2$O per gram Rh per hour.

EXAMPLE 10

250 g methyl acetate, 1.6 g RhCl$_3$.3H$_2$O, 10 g Re$_2$(CO)$_{10}$, 90 g CH$_3$I, 30 g acetic acid and 80 g 3-picolinium acetate were placed in a Hastelloy autoclave and reacted therein under a pressure of 80 bars at 435° K. with a mixture of 60 volume % CO and 40 volume % H$_2$. After a reaction period of 17 minutes, 158 g of a mixture of 63.2 mass % 1,1-diacetoxyethane and 36.8 mass % acetic anhydride was separated from the reaction product. This corresponded to a catalyst efficiency of 564 g 1,1-diacetoxyethane per gram Rh per hour and 328 g Ac$_2$O per gram Rh per hour.

EXAMPLE 11

250 g methyl acetate, 2.5 g Pd(OAc)$_2$, 8 g Re$_2$(CO)$_{10}$, 90 g CH$_3$I, 30 g acetic acid and 60 g N,N-dimethylimidazolium iodide were placed in a Hastelloy autoclave and reacted therein under a pressure of 80 bars at 450° K. with a mixture of 60 volume % CO and 40 volume % H$_2$. After a reaction period of 21 minutes, 151 g of a mixture of 89.3 mass % 1,1-diacetoxyethane and 10.7 mass % acetic anhydride was separated from the reaction product. This corresponded to a catalyst efficiency of 325 g 1,1-diacetoxyethane per gram Pd per hour and 39 g Ac$_2$O per gram Pd per hour.

We claim:

1. A process for making 1,1-diacetoxyethane by reacting methyl acetate or dimethylether with carbon monoxide and hydrogen under anhydrous conditions, at temperatures of 350° to 575° K., under pressures of 1 to 300 bars, and in the presence of a catalyst system containing noble metals belonging to group VIII of the periodic system of the elements, or compounds thereof, and iodine or its compounds, which comprises: effecting the reaction in the presence of said catalyst system containing, as additional ingredients, an aliphatic carboxylic acid having 1 to 8 carbon atoms, a manganese or rhenium compound and a heterocyclic aromatic compound selected from the group consisting of N-methylpyridinium iodide; N,N-dimethylimidazolium iodide; N-methyl-3-picolinium iodide; N-methyl-2,4-lutidinium iodide; N-methyl-3,4-lutidinium iodide; N-methylquinolinium iodide; pyridinium acetate; N-methylimidazolium acetate; 3-picolinium acetate; 2,4-lutidinium acetate and 3,4-lutidinium acetate.

2. A process as claimed in claim 1, wherein the ingredients of the catalyst system comprised of noble metal (compound)/manganese or rhenium compound/iodine (compound)/carboxylic acid/heterocyclic compound are used, respectively, in an atomic or molar ratio of 1:(0.1–10):(1–1400):(10–2000):(1–1200).

3. A process as claimed in claim 1, wherein a carbon monoxide/hydrogen mixture containing 25 to 75 volume % of hydrogen is used.

* * * * *